United States Patent [19]

Kratky

[11] Patent Number: 5,379,079
[45] Date of Patent: Jan. 3, 1995

[54] ATTACHMENT DEVICE FOR AN EXOPHTHALMOMETER

[75] Inventor: Vladimir Kratky, Kingston, Canada

[73] Assignee: Mount Sinai Hospital Corporation, Toronto, Canada

[21] Appl. No.: 5,427

[22] Filed: Jan. 19, 1993

Related U.S. Application Data

[63] Continuation of Ser. No. 698,027, May 10, 1991, abandoned.

[51] Int. Cl.$^6$ .............................................. A61B 3/10
[52] U.S. Cl. .................................. 351/204; 351/205; 351/245
[58] Field of Search ............... 351/204, 205, 243, 245; 128/23

Primary Examiner—William L. Sikes
Assistant Examiner—Hung Xuan Dang
Attorney, Agent, or Firm—Bereskin & Parr

[57] ABSTRACT

An attachment device for use with an exophthalmometer. The attachment device comprises positioning means attached to the exophthalmometer for abutting the forehead and nasion of the patient. The positioning means are adjustable for adjustably positioning the exophthalmometer on the face of the patient to permit measurement of exophthalmos in the absence of intact lateral orbital rims in a patient.

9 Claims, 4 Drawing Sheets

ATTACHMENT DEVICE FOR AN EXOPHTHALMOMETER

This is a continuation of application Ser. No. 07/698,027 filed May 10, 1991 now abandoned.

BACKGROUND OF THE INVENTION

Exophthalmos is generally understood to be the anterior displacement of the eyeball in relation to the cranium. Exophthalmos which can be unilateral or bilateral, may occur in a variety of different conditions; for example, endocrine imbalances, in particular hyperthyroidism or Graves' disease; intraorbital tumors; and, various space occupying processes in the orbit.

Exophthalmos can be measured with instrumental help using an exophthalmometer. The exophthalmometer is used to record any of three categories of exophthalmos. The first is absolute, where the measurement is compared with a known normal value. The second is relative exophthalmos, where a comparison is made of the measurement between the two eyes in the same individual, and the third is comparative exophthalmos where measurements in the same individual are compared from time to time. The degree of exophthalmos is generally measured by determining the extent of protrusion of the corneal apex from some reference point on the cranium. Most of the known exophthalmometers have employed the lateral orbital rim (i.e. outside bony wall of the eye socket) as a reference point and measure in an anterior-posterior plane the distance between the lateral orbital rim to the corneal apex with the eyes looking straight ahead.

The Hertel exophthalmometer (Hertel, E., Arch. F. Ophth. 60:171, 1905) is the most commonly used measurement instrument since it is cost-effective and relatively easy to learn and apply. Large population studies using the Hertel have provided normal range statistics for protrusion of the eyes and over time these have become the standard in orbital disease literature and an integral part of orbital examination. (For example, see Glaser, J. S., Orbital Disease and Neuro-Ophthalmoloy. In Tasman, W., and Jaeger, E. A., (Ed): Duane's Clinical Opthalmology; Vol. 2, Ch. 14, p. 6-7; J. B. Lippincott, Philadelphia, 1990; Young, I. S., and Henkind, P.: Medical Aspects of Graves' Opthalmopathy, In Smith, B. C., (Ed): Ophthalmic Plastic and Reconstructive Surgery; Vol. 2, Ch. 75, p. 1364, C. V. Mosby, St. Louis 1987; and Rootman, J.: Pathophysiologic Approach to Clinical Analysis of Orbital Disease, In Rootman, J., (Ed): Diseases of the Orbit, Ch. 6, p. 84, J. B. Lippincott, Philadelphia, 1988).

The Hertel exophthalmometer is a binocular instrument which rests on each lateral orbital rim and allows an observer in front, with the aid of mirrors to view images of the corneal apex of the two eyes as seen in profile superimposed upon a millimeter scale. A measurement is obtained of the relative distance of the apex of the cornea from a zero reference point, i.e., an imaginary horizontal line in a plane parallel to the front of the patient's face uniting the lateral orbital rims.

Several instruments with reference points other than the lateral orbital rims have been proposed (See Drews, 1956, Trans. Am. Ophthl. Soc. 54:215) but none of these instruments are in general use. For example, superior and inferior orbital margins have been proposed as reference points by Cohn (Jb. d. Schles. Ges. F. Enterl. Kultur 43:156, 1865; Klin. Mbl. Augenbeilk 5:339, 1867; and It'I Int. Cong. Ophthal. Paris 21, 1867), Landolt (1874), Mutch (Brit. J. Ophthal. 23:677, 1939) and Naugle (Proc. VIIth Congress European Soc. Ophthal. Helsinki 549, 1985). Watson in 1967 (Trans. Ophthal. Soc. U.K. 87;409) designed a device to fit over the nose and orbital tubercles.

Instruments, such as the Hertel exophthalmometer, which measure from the lateral orbital rims, are not useful for measuring exophthalmos in cases such as some endocrine exophthalmos where tissue edema can cause extensive swelling in the periorbital soft tissues or in all cases where there has been any disease, trauma, surgery or congenital anomaly affecting the lateral orbital rims. For example, the Hertel can not be used postoperatively in the case of a lateral orbitotomy which is used routinely for the removal of orbit tumors and Graves' orbital surgery.

In view of the above-mentioned limitations in exophthalmometers, stereophotogrammetric and radiographic techniques have been developed. (Beard, L. F. et al; A Straightforward Approach to Stereometric Photography for Medical Purposes, p. 27-48, In Herron, R. E. (ed). Biostereometrics 74, Falls Church, Va., and Backlund E. O. and Torlegard, K., Acta Opthalmol. (Copenh) 1968; 46(3): 575-579; Tengroth, B., Acta. Ophthalmol (Copenh) 1964); 42(4): 855-863; Borgen, H. G. et al., Trans. Am. Acad. Opthalmol. Otolaryngol, 1976, March-April, 81(2): 298-304; and Bogren, H., and Tengroth, B.; Clin. Radiol. 1967 April: 18(2); 193-196). The drawback to these techniques is that they require lengthy evaluation procedures and complex instrumentation.

SUMMARY OF THE INVENTION

The present invention provides an attachment device for use in combination with an exophthalmometer for use in the measurement of exophthalmos in a patient. The attachment device is particularly useful for measuring exophthalmos in a patient having alterations, variations or anomalies in their orbital rim(s). The attachment device of the invention may be attached to or integral with an exophthalmometer, particularly a binocular exophthalmometer, most particularly a Hertel exophthalmometer. The device of the present invention provides support for the exophthalmometer and provides a reference point for the measurement of exophthalmos in the absence of intact orbital rims in a patient. Thus, the attachment device will allow the physician to make surgical and diagnostic decisions, to follow up therapy or surgery, or to investigate congential anomalies in cases where hitherto known instruments are of limited assistance.

The device of the present invention also has the advantage that the measurement of exophthalmos is done by using the exophthalmometer i.e. in the case of a Hertel exophthalmometer images of the corneal apex of the eyes as seen in profile superimposed upon a millimeter scale are viewed, and the investigator is not required to learn a new technique or a new set of standards.

The invention thus provides an attachment device for use with an exophthalmometer comprising positioning means mountable on said exophthalmometer for abutting the forehead and nasion of a patient, said positioning means being adjustable for adjustably positioning said exophthalmometer on the face of the patient to permit measurement of exophthalmos in the absence of intact lateral orbital rims in a patient.

The positioning means comprises a forehead engaging member adapted to abut the patient's forehead, and a nasion-engaging member shaped to abut the nasion of the patient. Preferably at least one of the forehead engaging member and the nasion-engaging member is adjustably mounted relative to said exophthalmometer for movement in a anterior-posterior direction perpendicular to the face of the patient and having calibration means for measuring the position of the forehead engaging member or the nasion-engaging member relative to said exophthalmometer. Further, the forehead engaging member provides two spaced apart contact points for contacting the patient's forehead.

The invention also provides an attachment device as described above in combination with an exophthalmometer, preferably a binocular exophthalmometer, most preferably a Hertel exophthalmometer. The exophthalmometer preferably comprises a shaft portion and two movable spaced apart carrier portions connected by the shaft portion, each carrier portion having a rim placement means to locate the carrier portion adjacent to the lateral orbital rim of a patient, a calibration scale, and a mirror inclined to reflect the calibration scale and the corneal apex of an eye of the patient whereby the corneal apex is superimposed on the calibration scale.

The term "exophthalmos" is generally understood to mean the anterior displacement of the eyeball in relation to the cranium. However, a measurement of exophthalmos is generally compared with a known normal value, with a measurement from the other eye in the same individual, or with a measurement in the same individual taken from time to time and a given measurement may be considered as exophthalmos or proptosis or as enophtholmos or sunken eye. For example, a measurement of 20-25 (right eye 20 mm-left eye 25 mm) may be looked at as right enophthalmos or left exophthalmos. The attachment device of the present invention in combination with an exophthalmometer may thus be used for measuring exophthalmos or enophthalmos in a patient.

BRIEF DESCRIPTION OF THE DRAWINGS

The invention will now be described with reference to the drawings wherein.

DETAILED DESCRIPTION OF THE INVENTION

Figure 1:
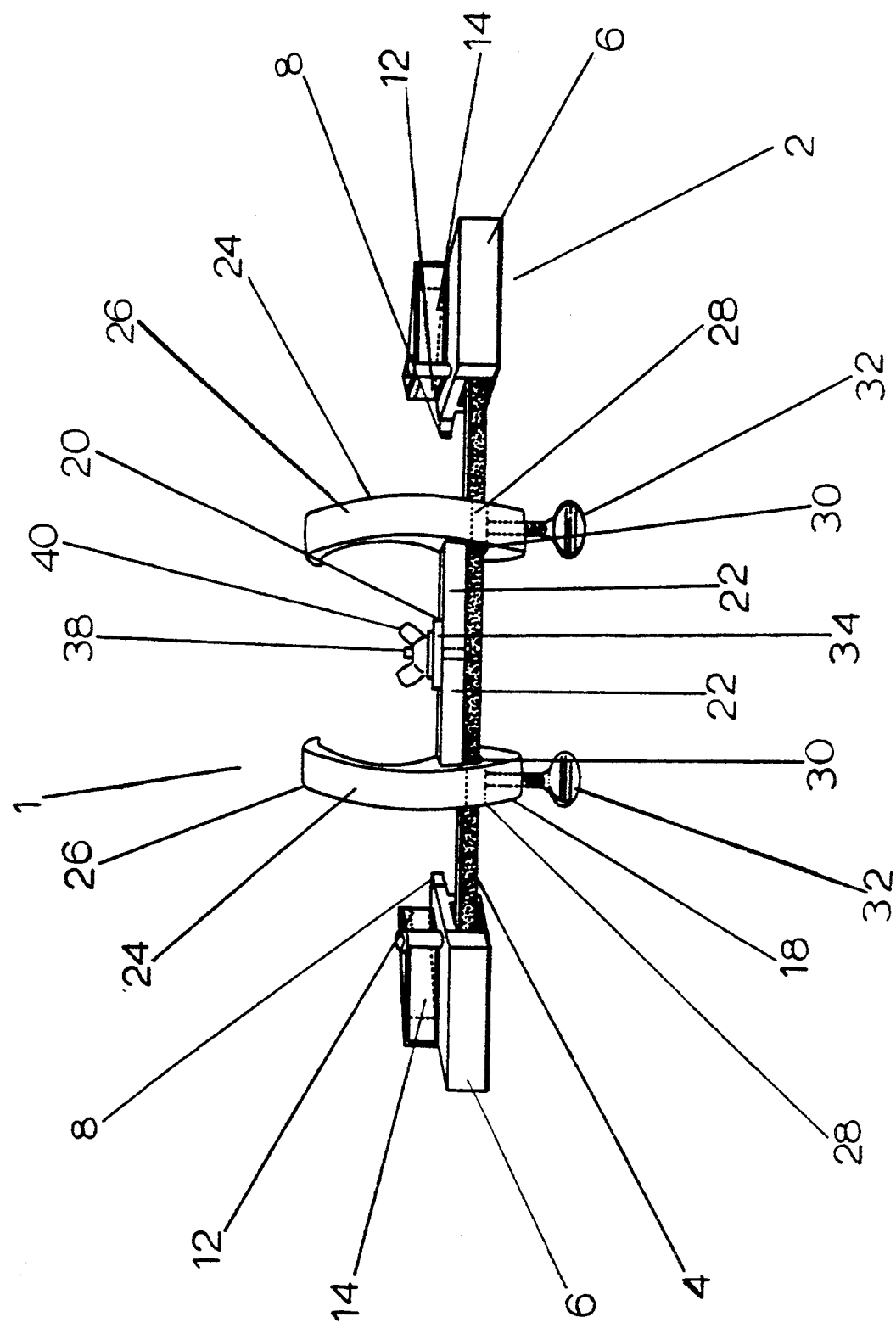
FIG. 1 is a front elevation view of an exophthalmometer with an attachment device of the present invention.
Figure 3:
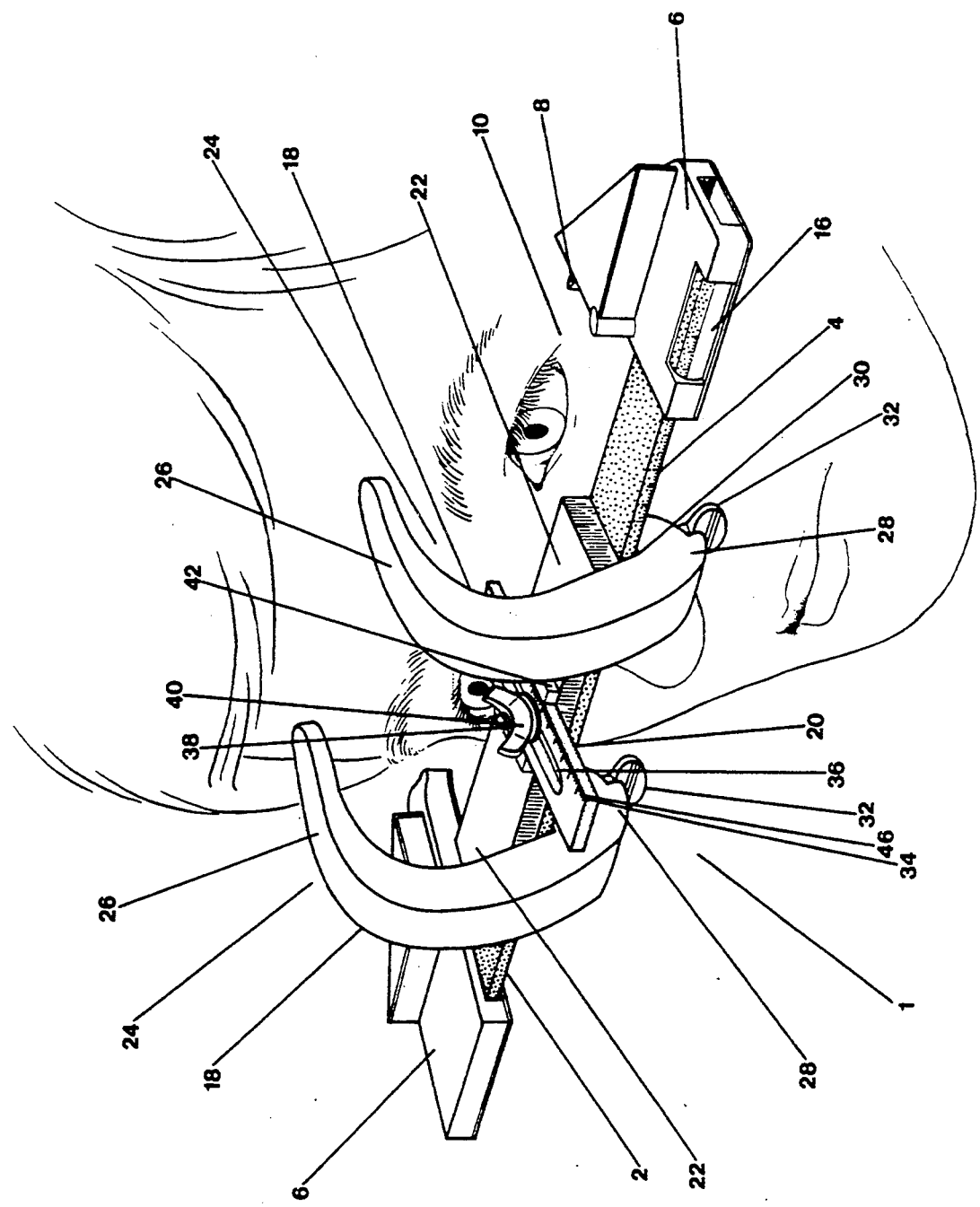
FIG. 3 is a perspective view of an exophthalmometer and an attachment device of the present invention in typical position on the face.
Figure 4:
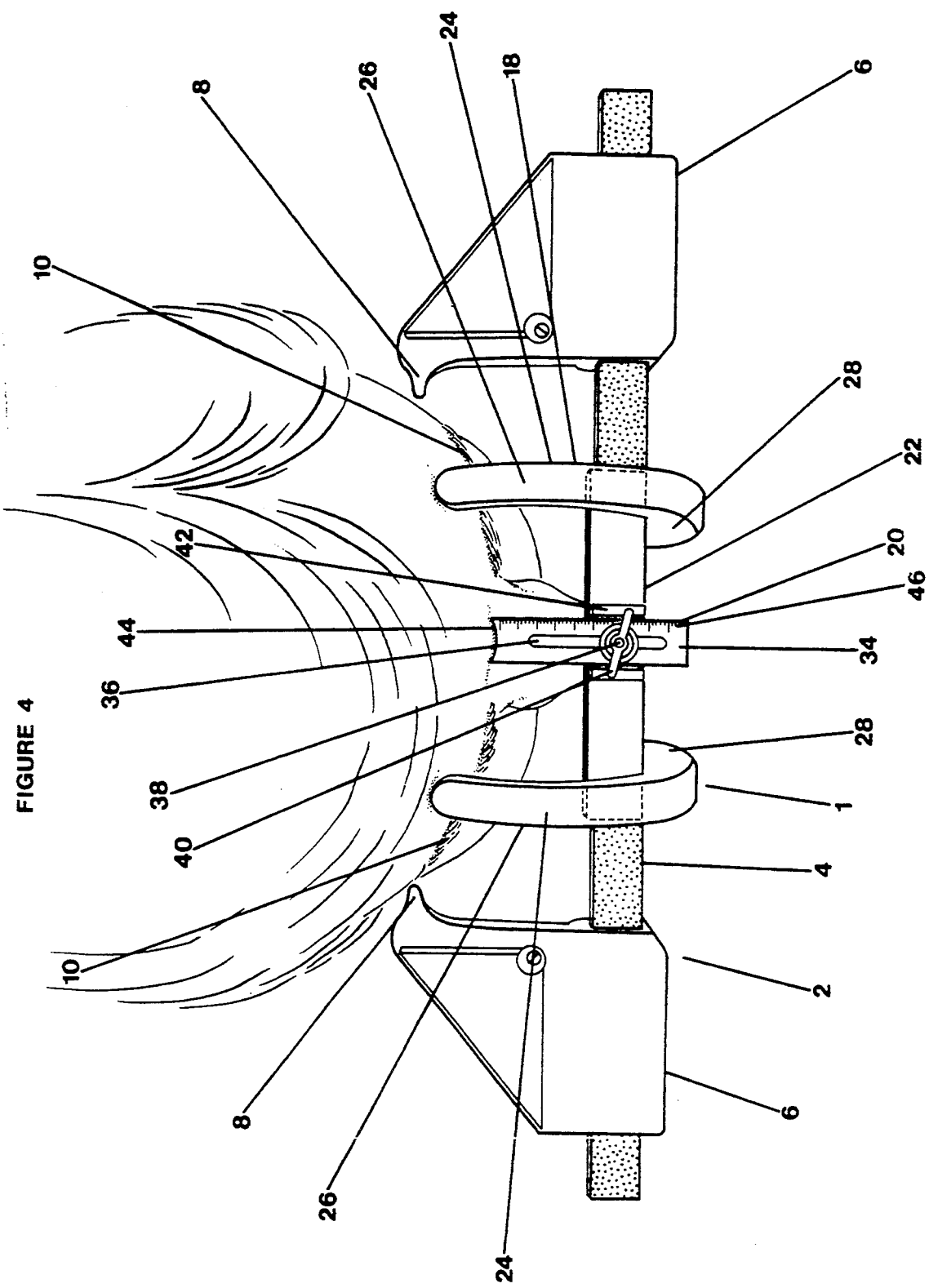
FIG. 4 is a top view of an exophthalmometer and an attachment device of the present invention in typical position on the face of a patient.

In the embodiments of the invention described and illustrated in FIGS. 1, 3 and 4, an exophthalmometer generally designated 2 is shown. The exophthalmometer 2 in a preferred embodiment is a binocular exophthalmometer, most preferably a Hertel exophthalmometer. The illustrated exophthalmometer 2 comprises a shaft portion 4 having two moveable spaced-apart carrier portions 6 connected by the shaft portion 4. The shaft portion 4 generally has the following dimensions: 1.5 cm width×0.5 cm height×23 cm length. Each of the carrier portions 6 have a rim placement means 8 to locate the carrier portions 6 adjacent to the lateral orbital rims 10 of a patient. The rim placement means 8 is preferably a notch. As shown in FIG. 1 the carrier portions 6 also have a calibration scale 12, preferably a millimeter scale, and a mirror 14 inclined to reflect the calibration scale 12 and a corneal apex of an eye of the patient. The mirror is preferably inclined at about 45°. In FIG. 3, a second calibration scale 16 which is used to calibrate the distance between the carrier portions 6 is shown.

In the embodiment of the invention described and illustrated in FIGS. 1, 3 and 4, an attachment device generally designated 1 is shown in attached relation to an exophthalmometer 2, preferably a binocular exophthalmometer, most preferably a Hertel exophthalmometer. The attachment device 1 generally comprises a forehead engaging member 18 which is adapted to abut a patient's forehead and which is mounted on the shaft portion 4 of the exophthalmometer 2 and a nasion-engaging member 20 shaped to abut the nasion of the patient. At least one of the forehead-engaging member 18 and the nasion-engaging member 20 are adjustably mounted for movement in an anterior-posterior direction perpendicular to the face of the patient and have calibration means for measuring the position of the forehead-engaging member 18 or nasion-engaging member 20 relative to the exophthalmometer 2.

Figure 2:
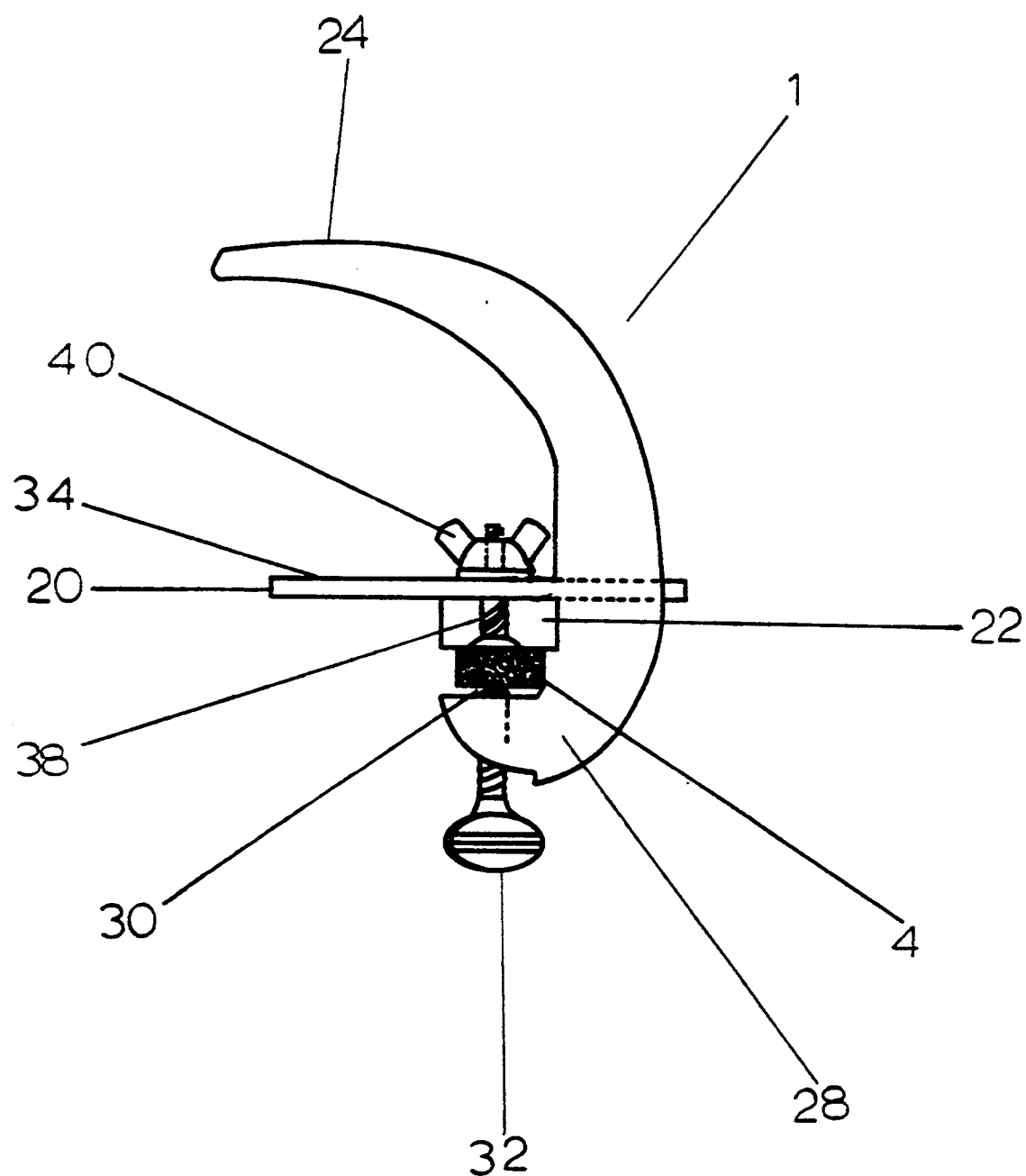
FIG. 2 is a side view of the shaft portion of an exophthalmometer and an attachment device of the present invention.

FIG. 2 shows the attachment device 1 described and illustrated herein in attached relation to the shaft portion 4 of an exophthalmometer.

In the attachment device 1 illustrated in FIGS. 1 to 4, the forehead-engaging member 18 comprises a horizontal bar 22 and two arcuate arms 24 disposed in parallel vertical planes and disposed on either side of the nasion-engaging member 20 connected by the horizontal bar 22. The horizontal bar 22 generally has the following dimensions: 0.5 cm (height)×1.5 cm (width)×8 cm (length). The arcuate arms 24 each have a top portion 26 which is adapted to abut a patient's forehead and a shaft attachment portion 28 distal to the top portion 26 for releasably mounting the forehead-engaging member 18 on the shaft portion 4 of the exophthalmometer 2. More particularly, the shaft attachment portion 28 forms a slot 30 to accept the shaft portion 4 of the exophthalmometer 2. The shaft attachment portion 28 preferably has releasable securing means 32 for securing the shaft portion 4 in slot 30. The securing means 32 may comprise a screw clamp as illustrated in FIGS. 1, 2 and 3 or other securing means including a clip, a spring-loaded clamp or quick release lever.

In the attachment device 1 illustrated in FIGS. 1 to 4, the nasion-engaging member 20 comprises a plate 34 having a centrally located elongated opening 36. The plate 34 is adjustably mounted on the horizontal bar 22. More particularly, a screw 38 is screwed in the horizontal bar 22 and passes through the elongated opening 36 to permit slidable movement of the plate 34 relative to the horizontal bar 22 and shaft portion 4. Plate securing means 40, in the form of a wing nut is provided engaging the projecting part of the screw 38 for securing the plate 34 in a fixed position relative to the horizontal bar 22. Preferably, guide bars 42 are located on the horizontal bar 22 to locate the plate 34 on the shaft portion 4 and to provide a guide for the sliding movement of the plate 34 relative to the horizontal bar 22 and the shaft portion 4.

The plate 34 as illustrated in FIGS. 1 to 4 has dimensions of about 6 cm×1.5 cm. Preferably the end of the plate 34 to be placed in contact with the nasion is shaped to fit the nasion; for example, the plate may have a curved recess 44. The plate has calibration means 46, preferably a millimeter scale, for measuring the position of the nasion-engaging member 20 relative to the exophthalmomoeter 2. The elongated opening 36 in the plate 34 is large enough to accept the screw 38 and has dimensions of about 40 mm×4 mm.

The attachment device 1 may be constructed from rigid materials including a plastic, such as acrylic and stainless steel.

The use of the attachment device i of the present invention in combination with an exophthalmometer 2 is described and illustrated in FIGS. 3 and 4. In use, the carrier portions 6 are adjusted so that the rim placement means 8 are placed adjacent to the lateral orbital rims 10 of the patient. The attachment device 1 is positioned about halfway between the carrier portions 6 of the exophthalmometer 2. The top portions 26 of the arcuate arms 24 of the forehead engaging member 18 are brought into contact with the forehead of the patient. The plate securing means 40 is adjusted such that the plate 34 is slidable in relation to the shaft portion 4 of the exophthalmometer 2. The plate 34 is slidable to rest on the nasion of the patient and the plate securing means 40 is then adjusted to prevent movement of the plate 34 relative to the shaft portion 4 of the exophthalmometer 2. A measurement of the position of the nasion-engaging member 20 relative to the exophthalmometer 2 may be recorded using the calibration means 46. The measurement can then be used in subsequent examinations to locate the exophthalmometer 2 in combination with the attachment device 1 on the face of the patient. When the exophthalmometer in combination with the attachment device is placed in position on the face of the patient, exophthalmos is measured in the usual manner using the exophthalmometer 2 i.e. viewing images of the corneal apex of the eyes as seen in profile superimposed upon the calibration scale 12.

The use of the attachment device 1 of the invention in combination with an exophthalmometer 2 will now be described by reference to some examples of clinical situations.

The attachment device 1 of the invention in combination with an exophthalmometer 2 may be used to record comparative exophthalmos where measurements made in the same individual are compared from time to time. For example, exophthalmos may be measured before and after a procedure which affects the orbital rims such as orbitotomy. Preoperatively a measurement is obtained using the procedure described above, of the position of the nasion-engaging member 20 relative to the shaft portion 4 of the exophthalmometer 2 while the forehead engaging member 18 abuts the forehead of the patient and the rim placement means 8 rest on the lateral orbital rims 10 of the patient. Postoperatively, the nasion-engaging member 20 is adjusted in accordance with the measurement taken preoperatively and the attachment device in combination with the exophthalmometer 2 is placed in position on the patient's face i.e. adjacent to the lateral orbital rims and abutting the nasion and forehead. The zero reference point for measuring exophthalmos i.e. the imaginary horizontal line in a plane parallel to the front of the patient's face uniting the orbital rims, remains the same preoperatively and postoperatively when the attachment device of the present invention is used in combination with the exophthalmometer thus permitting comparative measurement of exophthalmos in the patient.

The attachment device of the invention in combination with an exophthalmometer 2 may be used to measure exophthalmos in a patient where only one lateral orbital rim is intact. A measurement is obtained of the position of the nasion-engaging member 20 relative to the shaft portion 4 of the exophthalmometer 2 while the forehead engaging member 18 is in contact with the patient's forehead, and the rim placement means 8 abuts the intact lateral orbital rim. Exophthalmos measurements recorded for the eye on the opposite side to the intact rim will use the intact rim as the zero reference value.

In the case where both lateral orbital rims are absent, an absolute zero reference point is not known. However, a measurement may be obtained in an individual patient using the attachment device 1 of the present invention in combination with an exophthalmometer, of the position of the nasion-engaging member 20 relative to the shaft portion 4 while the forehead engaging member 18 abuts the patient's forehead, and the rim placement means 8 are located adjacent to the lateral orbital rims 10 of the patient. The measurement may then be used in subsequent examinations to place the exophthalmometer in the same position on the individual thus permitting determinations of the variation in exophthalmos in the same patient from time to time, for example, during treatment.

While the embodiments above described in connection with FIGS. 1 to 4 are preferred, there are of course modifications that can be made thereto, that are within the contemplation of the present invention. As an example, the forehead engaging member 18 of the attachment device 1 may be a Y-shaped arm or a headband. Also, the attachment device 1 may be constructed so that it is integral with the exophthalmometer 2. The attachment device 1 in combination with the attachment device may also be constructed as a free-standing instrument. Further, the forehead engaging member 18 and the nasion-engaging member 20 may be independently mounted on the shaft portion 4 of the exophthalmometer 2. In other respects as well, a latitude of modification, change and substitution is intended in the foregoing disclosure and in some instances some features of the invention will be employed without a corresponding use of other features.

The following examples are illustrative of the present invention:

EXAMPLES

Exophthalmos was measured in patients using a Hertel exophthalmometer, and the attachment device of the present invention, as illustrated in FIGS. 1 to 4, in combination with the Hertel exophthalmometer. When the Hertel exophthalmometer alone was used it was rested, where possible, on each lateral orbital rim of the patient and a measurement was obtained of the relative distance of the apex of the cornea from the zero reference point i.e. an imaginary horizontal line in a plane parallel to the front of the patient's face uniting the lateral orbital rims. The attachment device in combination with the Hertel exophthalmometer was placed in position on the patient's face i.e. the carrier portions were adjacent to the lateral orbital rims and the attachment device abutted the forehead and nasion of the patient. The nasion-engaging member on the attachment device was set at 15 mm for all patients except where otherwise stated.

a) Patient M.T. had facial trauma including broken orbital rims. Postoperatively the Hertel gave a measurement of 20-21 (giving the appearance that the left eye protrudes over right eye by 1 mm) using the attachment device in combination with the Hertel the frontal plane of measurement was maintained and a measurement of 33-25 mm (right eye protrudes over left by 8 mm) was recorded. The Hertel gave a false reading of nearly equal position. However, the attachment device revealed 9 mm of exophthalmos.

b) Patient A. H. had left orbital trauma. The Hertel gave a measurement of 17-15 (Right protrudes by 2 mm) and with the attachment device (nasion-engaging member set at 20 mm) gave a measurement of 26-22 (Right protrusion by 4 mm). The Hertel underestimated left enophthalmos by 2 mm, as shown by the attachment device. The measurement obtained using the attachment device indicated corrective surgery.

c) Patient G. A. had trauma to the right orbit. The Hertel gave a measurement of 13-15 (Left protrudes by 2 mm) and with the attachment device of the invention gave a measurement of 22-18 (Right protrudes by 4 mm). The Hertel findings suggested right enophthalmos (sunken eye); the Hertel with the attachment device showed that the right eye in fact protruded by 4 mm.

d) Patient D. A. had trauma to the right face and showed a clinical appearance ('eyeballing it') of right enophthalmos (sunken eye). Plastic surgery was planned to correct the condition. The attachment device with nasion-engaging member set at 20 mm gave a measurement of 28-25 (Right protrudes by 3). Thus, the Hertel with the attachment device showed that the right eye was not enophthalmic, but protruded by 3 mm and surgical correction was in fact contraindicated.

e) Patient J. O. had trauma to the left rim and the investigator was unable to use the Hertel because of tissue swelling etc. The Hertel with the attachment device with nasion-engaging member set at 20 mm gave a measurement of 24-24 (equal). The Hertel with the attachment device showed that the eyes are equally positioned in the sockets and thus corrective surgery was not indicated.

f) Patient J. J. had congenital hypoplastic (maldeveloped) orbit and the investigator was unable to use the Hertel due to asymmetry of the skull. The Hertel with the attachment device with nasion-engaging member set at 20 showed that the left eye protruded by 3 mm. This information can be used for planning corrective surgery.

g) Patient J. C. had Graves (thyroid) disease and surgery was performed to correct protrusion of the eyes. Measurements were obtained pre- and postoperatively in order to determine the success of the operation. Preoperatively the Hertel showed left protrusion by 3 mm (23-26). Postoperatively, using the Hertel with the attachment device, the left eye was found to be sunken by 2 mm (25-27) compared to the right eye, which is a total of 5 mm decompressive effect from surgery. The Hertel could not be used in postoperative readings because the rim was removed. The measure of decompressive effect was not possible without the use of the attachment device.

h) Patient F. J. had previous left rim removal for Graves disease. She was worried that the left eye appeared to protrude again. The attachment device showed that the two eyes were in equal positions (32-32).

i) Patient A. G. had Graves disease and surgical treatment was performed to remove the left rim. Measurements were taken postoperatively to determine how much the surgery moved the eye back. Postoperatively, the Hertel with the attachment device gave a measurement of 22-25 (left protrusion by 3 mm) and showed that the difference between the eyes was decreased to 3 mm from the pre-operative value of 10 (18-28 left protrusion by 10 mm) measured using the Hertel alone (i.e. decompressive effect of 7 mm).

j) Patient B. F. had Graves disease and had a bilateral rim removal. Preoperatively the Hertel alone gave a measurement of 26-24 and pre-operatively the Hertel with the attachment device gave a measurement of 37-35 (i.e. conversion factor of 11=37 minus 26, 35 minus 24). Postoperatively the Hertel with the attachment device gave a measurement of 29-28. Using the conversion factor, this reading translates to 18-17 for the Hertel alone i.e. 29 minus 11, 28 minus 11. The Hertel with the attachment device showed the decompressive effect to be 8 mm on the right and 7 mm on the left. The absolute position of the eyes postoperatively using the Hertel alone was calculated as 18-17 using the conversion factor. This absolute 18-17 measurement may be compared to the measurements obtained for population studies using the Hertel alone.

k) Patient G. R. had left orbital trauma and therefore the left orbital rim could not be used to measure exophthalmos. The Hertel gave a measurement of 13-11 (Right protrudes by 2 mm) and with the attachment device gave a measurement of 19-17 (Right protrudes by 2 mm). The attachment device confirmed right protrusion by 2 mm. In this case, the attachment device confirmed that there was insignificant orbital displacement and thus confirmed that the Hertel reading was a true reading.

I claim:

1. An attachment device for use with an exophthalmometer comprising positioning means mountable on said exophthalmometer for abutting the forehead and nasion of a patient, said positioning means being adjustable for adjustably positioning said exophthalmometer on the face of the patient to permit measurement of exophthalmos in the absence of intact lateral orbital rims in a patient, wherein the positioning means comprises a forehead engaging member including at least two laterally spaced apart contact points adapted to abut the patient's forehead and a nasion-engaging member shaped to abut the nasion of the patient, to provide a stable three point support.

2. An attachment device as claimed in claim 1, wherein at least one of the forehead engaging member and the nasion-engaging member is adjustably mounted relative to said exophthalmometer for movement in an anterior-posterior direction perpendicular to the face of the patient and has calibration means for measuring the position of the forehead engaging member or the nasion-engaging member relative to said exophthalmometer.

3. The attachment device as claimed in claim 2, wherein the forehead engaging member comprises two arcuate arms disposed in parallel vertical planes on either side of said nasion-engaging member, said arcuate arms having a top portion adapted to abut the patient's forehead and a shaft attachment portion distal to said top portion for releasably attaching said arcuate arms to said exophthalmometer.

4. An attachment device as claimed in claim 3, wherein the nasion-engaging member is adjustably mounted on the exophthalmometer for movement in an anterior-posterior direction perpendicular to the face of the patient and has calibration means for measuring the position of the nasion-engaging member relative to said exophthalmometer.

5. The attachment device as claimed in any one of claims 1, 2, 3 and 4 which is integral with said exophthalmometer.

6. An attachment device as claimed in claim 3, wherein the two arcuate arms are connected by a horizontal bar and the nasion engaging member is adjustably mounted on the horizontal bar for movement in an anterior-posterior direction perpendicular to the face of the patient and has calibration means for measuring the position of the nasion-engaging member relative to said exophthalmometer.

7. An attachment device as claimed in claim 6, wherein the nasion-engaging member comprises a plate having a centrally located elongated opening said plate being mounted on the horizontal bar by means of a screw which is attached to the horizontal bar and passes through the elongated opening.

8. An attachment device as claimed in claim 7, wherein plate securing means are provided on the screw for securing the plate in a fixed position relative to the horizontal bar.

9. An attachment device as claimed in any one of claims 1, 2 and 3 to 8 in combination with an exophthalmometer comprising a shaft portion having two movable spaced apart carrier portions connected by the shaft portion, each carrier portion having a rim placement means to locate the carrier portion adjacent to the lateral orbital rim of a patient, a calibration scale, and a mirror inclined to reflect the calibration scale and the corneal apex of an eye of the patient whereby the corneal apex is superimposed on the calibration scale.

* * * * *